US00PP25655P3

(12) United States Plant Patent
Radler

(10) Patent No.: US PP25,655 P3
(45) Date of Patent: Jun. 30, 2015

(54) GRANDIFLORA ROSE PLANT NAMED 'RADTREASURE'

(50) Latin Name: *Rosa hybrida*
Varietal Denomination: Radtreasure

(71) Applicant: CP DELAWARE, INC., Wilmington, DE (US)

(72) Inventor: William J. Radler, Greenfield, WI (US)

(73) Assignee: CP Delaware, Inc., Wilmington, DE (US)

( * ) Notice: Subject to any disclaimer, the term of this patent is extended or adjusted under 35 U.S.C. 154(b) by 71 days.

(21) Appl. No.: 13/998,766

(22) Filed: Dec. 4, 2013

(65) Prior Publication Data

US 2015/0156931 P1 Jun. 4, 2015

(51) Int. Cl.
*A01H 5/02* (2006.01)

(52) U.S. Cl.
USPC ..... Plt./137

(58) Field of Classification Search
USPC ..... Plt./137, 136, 138
CPC ..... A01H 5/0222; A01H 5/0216
See application file for complete search history.

*Primary Examiner* — Kent L Bell
(74) *Attorney, Agent, or Firm* — Buchanan, Ingersoll & Rooney PC

(57) ABSTRACT

A new and distinct Grandiflora rose plant is provided that abundantly and substantially continuously forms attractive semi-double deep salmon pink blossoms. The plant exhibits vigorous vegetation and an upright and bushy growth habit. The foliage is dense dark green with a semi-glossy finish on the upper surface. The deep salmon pink blossom coloration contrasts nicely with the dark green foliage. The disease resistance has been found to be very good during observations to date. The plant is well suited for providing attractive ornamentation in in the landscape. The new plant during observations has displayed an advantageous combination of characteristics, such as strong blossom color, a good overall growth habit, an abundant flowering density, a propensity to rebloom, and the absence of disease.

1 Drawing Sheet

Botanical/commercial classification: *Rosa hybrida*/Grandiflora Rose Plant.

Varietal denomination: cv. Radtreasure.

SUMMARY OF THE INVENTION

The new variety of *Rosa hybrida* Grandiflora rose plant was created at Greenfield, Wis., U.S.A., by artificial pollination wherein two parents were crossed which previously had been studied in the hope that they would contribute the desired characteristics. The female parent (i.e., the seed parent) was the 'Radraztwice' variety (non-patent in the United States). The male parent (i.e., the pollen parent) was the 'Radfab' variety (non-patented in the United States).

The parentage of the new variety can be summarized as follows:

'Radraztwice'×'Radfab'.

The seeds resulting from the above pollination were sown and small plants were obtained which were physically and biologically different from each other. Selective study resulted in the identification of a single plant of the new variety.

It was found that the new Grandiflora rose plant of the present invention possesses the following combination of characteristics:

(a) abundantly forms on a substantially continuous basis attractive double deep salmon pink blossoms,
(b) exhibits an upright and bushy growth habit,
(c) forms vigorous vegetation, (d) forms attractive dense dark green foliage with a semi-glossy finish on the upper surface that contrasts well with the blossom coloration,
(e) exhibits very good disease resistance, and
(f) is well suited for growing as attractive ornamentation in the landscape.

The new Grandiflora variety is considered to be indicative of a breakthrough in rose breeding as one of the first garden roses with all of the attributes of a quality landscape shrub rose—strong color, good habit, good flowering density, good propensity to rebloom, and very good disease resistance. The plant has been observed to be hardy to U.S.D.A. Hardiness Zone No. 5.

The new variety well meets the needs of the horticultural industry. It can be grown to advantage as ornamentation in parks and gardens.

The new variety can be readily distinguished from its parents through an inspection of the blossoms and the overall growth habits. For instance, the blossoms of the new variety are deeper in coloration, larger, and display a greater number of petals. Also, the new variety exhibits a fuller, more dense growth habit than either parent. Furthermore, each parent forms semi-double blossoms unlike the double blossoms of the new variety.

The new variety of the present invention also can be readily distinguished from other Grandiflora rose plants including the 'Meikanaro' variety (U.S. Plant Pat. No. 23,551) through an inspection of the blossoms. For instance, the deep salmon pink blossoms of the new variety are dissimilar in color to the yellow finishing to cream blossoms of the 'Meikanaro' variety. Also, the foliage of the 'Meikanaro' variety is glossy on the upper surface while that of the new variety is semi-glossy.

The characteristics of the new variety have been found at Wasco, Calif., U.S.A., to be homogeneous and stable and to be strictly transmissible by asexual propagation, such as budding, grafting, and the rooting of cuttings from one generation to another. The new variety reproduces in a true-to-type manner by such asexual propagation.

The new variety has been named 'Radtreasure', and is being marketed under the TAHITIAN TREASURE trademark.

BRIEF DESCRIPTION OF THE PHOTOGRAPHS

The accompanying photographs show, as nearly true as it is reasonably possible to make the same in color illustrations of this character, typical flowering rose plants of the new variety. The illustrated rose plants of the new variety were approximately two years of age and were observed during May 2012, while growing outdoors on their own roots at Davis, Calif., U.S.A.

DETAILED BOTANICAL DESCRIPTION

Figure 1:
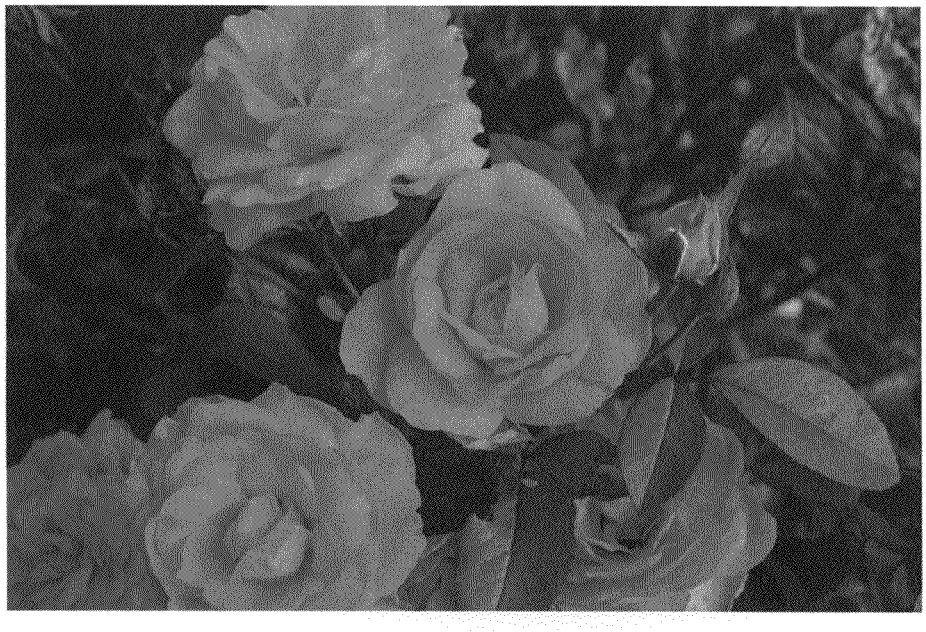
FIG. 1 shows a close view of the attractive double deep salmon pink blossoms of the new variety. Dark green foliage and a typical flower bud also are included.
Figure 2:
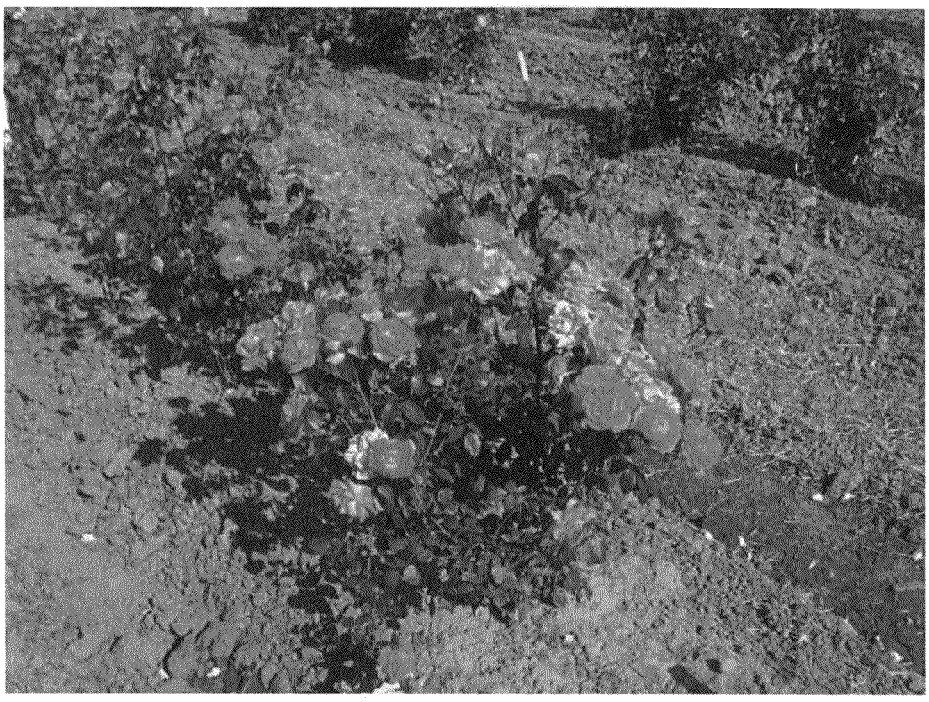
FIG. 2 shows at the forefront a view of a row of blossoming Grandiflora rose plants of the new variety.

The chart used in the identification of colors is that of The Royal Horticultural Society (R.H.S. Colour Chart—1995 Edition or equivalent), London, England. The description is based on the observation of two-year-old specimens of the new variety during September 2013 while growing in containers outdoors on their own roots at West Grove, Pa., U.S.A. Class: Grandiflora. Cultivar 'Radtreasure'.

Plant:

*Height*.—Approximately 1.6 m on average at full maturity.

*Width*.—Approximately 1.3 m on average at full maturity.

*Habit*.—Upright and bushy.

Branches:

*Color*.—A blend of near Greyed-Purple Group 183D and Greyed-Green Group 191A on young stems, and commonly near Green Group 137B on mature wood.

*Texture*.—Smooth.

*Thorns*.—Size: on young stems commonly approximately 6 mm in length on average and approximately 2 mm in width on average, and on adult stems commonly approximately 8 mm in length on average and approximately 6 mm in width on average. Quantity: moderate. Color: commonly near Greyed-Purple Group 183C on young stems, and near Greyed-Brown Group 199A when mature.

Leaves:

*Size*.—Commonly approximately 10.5 cm in length on average and approximately 7.3 cm in width on average for a seven-leaflet leaf.

*Leaflets*.—Number 3, 5, and 7 (most often). Length: approximately 5.2 cm on average for a terminal leaflet. Width: approximately 2.7 cm on average for a terminal leaflet. Shape: generally oval. Apex: acuminate. Base: rounded. Margins: slightly denticulate, small and single. Texture: generally smooth. Overall appearance: attractive dark green leaves with a semi-glossy upper surface. Color: (when young): Upper surface: near Green Group 143B. Under surface: near Green Group 143C. Color (when fully mature): Upper surface: near Green Group 139A. Under surface: near Greyed-Green Group 191A.

*Petioles*.—Length: approximately 1.5 cm on average. Diameter: approximately 1 mm on average. Texture: smooth. Color: near Green Group 139A overlaid with Greyed-Purple Group 183D.

*Rachis*.—Color: near Greyed-Green Group 191A.

*Stipules*.—Size: approximately 1.3 cm in length on average and approximately 1 mm in width on average. Color: on the upper surface near Green Group 139A overlaid with near Greyed-Purple Group 139A, and on the under surface near Yellow-Green Group 146B.

Inflorescence:

*Number of flowers*.—Commonly one per stem or up to approximately 3 blooms in a cluster.

*Peduncle*.—Commonly a blend of Greyed-Purple Group 183D and Greyed-Green Group 191A in coloration, commonly approximately 4.5 cm in length on average, and approximately 2 mm in diameter on average.

*Sepals*.—Shape: lanceolate with a truncate base. Margins: with extensions and smooth between extensions. Texture: on the upper surface covered with short pubescence, and smooth on the under surface. Size: commonly approximately 2.8 cm in length on average, and approximately 8 mm in width at the base. Number: five. Color: on the upper surface Greyed-Purple Group 183A, and on the under surface Yellow-Green Group 144A overlaid with Greyed-Purple Group 183A.

*Buds*.—Shape: generally ovoid. Length: approximately 2 mm on average as the calyx breaks. Diameter: approximately 1.3 cm on average as the calyx breaks. Color: near Red Group 54A.

*Flower*.—Form: double, cuplike. Diameter: commonly approximately 8 cm on average. Height: commonly approximately 4.5 cm on average. Color (in course of opening): Upper surface: near Red Group 56D at the point of attachment, transitioning to Red Group 55A at the apex. Under surface: near Red Group 55D at the point of attachment blending to Red-Purple Group 61 D at the apex. Color (when open): Upper surface: near Red Group 49D at the point of attachment, transitioning to Red Group 49C, and finally to Red-Purple Group 58B at the apex. Under surface: near Red Group 55B at the point of attachment blending to Red-Purple Group 58C at the apex. Color stability: excellent, with most petals fading slightly with full maturity. Fragrance: slight. Petal number: commonly approximately 50 to 60 on average under normal growing conditions. Petal arrangement: imbricated. Petal length: commonly approximately 4.1 cm on average. Petal width: commonly approximately 4 cm on average. Petal shape: generally oval. Petal margin: entire, slightly recurved. Petal texture: smooth on both surface. Petal apex: rounded. Petal base: rounded. Petal drop: good, the petals commonly detach cleanly and freely drop upon full maturity. Stamen number: approximately 90 on average. Anthers: approximately 2 mm in length, approximately 1 mm in diameter, and the coloration is near Yellow-Orange Group 21A. Filaments: approximately 5 mm in length, less than 1 mm in diameter, and the coloration is near Yellow Group 11D. Pollen:

commonly present in a moderate quantity and near Yellow Group 13C in coloration. Pistils: approximately 103 on average. Styles: commonly range in length from approximately 3 to 7 mm, less than 1 mm in width, the lower ⅔s is near Yellow Group 8D in coloration, and the upper ⅓ is near Red-Purple Group 58B in coloration. Stigma: commonly less than 1 mm in size, and, near Yellow-Orange Group 22A in coloration. Receptacle: commonly oval in shape, approximately 1 cm in length on average, approximately 7 mm in width on average, smooth in texture, and near Yellow-Green Group 144A in coloration. Hips/seeds: none observed to date.

Development:

*Vegetation*.—Vigorous and strong.

*Blossoming*.—Early season, abundant and substantially continuous from spring to first frost.

*Resistance to diseases*.—Very good during observations to date.

Plants of the 'Radtreasure' variety have not been observed under all possible environmental conditions to date. Accordingly, it is possible that the phenotypic expression may vary somewhat with changes in light intensity and duration, cultural practices, and other environmental conditions.

I claim:

1. A new and distinct Grandiflora rose plant characterized by the following combination of characteristics:

(a) abundantly forms on a substantially continuous basis attractive double deep salmon pink blossoms, (b) exhibits an upright and bushy growth habit, (c) forms vigorous vegetation, (d) forms attractive dense dark green foliage with a semi-glossy finish on the upper surface that contrasts well with the blossom coloration, (e) exhibits very good disease resistance, and (f) is well suited for growing as attractive ornamentation in the landscape;

substantially as herein illustrated and described.

* * * * *